United States Patent
Su et al.

(10) Patent No.: US 11,406,347 B2
(45) Date of Patent: Aug. 9, 2022

(54) ACOUSTIC MONITORING TO DETECT MEDICAL CONDITION

(71) Applicant: Medtronic, Inc., Minneapolis, MN (US)

(72) Inventors: Xin Su, Plymouth, MN (US); Timothy J. Denison, Minneapolis, MN (US); Brett Knappe, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 883 days.

(21) Appl. No.: 14/920,363

(22) Filed: Oct. 22, 2015

(65) Prior Publication Data
US 2016/0113618 A1    Apr. 28, 2016

Related U.S. Application Data

(60) Provisional application No. 62/067,817, filed on Oct. 23, 2014.

(51) Int. Cl.
*A61B 7/00*    (2006.01)
*A61B 5/00*    (2006.01)
*A61B 7/02*    (2006.01)

(52) U.S. Cl.
CPC ............ *A61B 7/003* (2013.01); *A61B 5/0002* (2013.01); *A61B 5/7275* (2013.01); *A61B 5/7282* (2013.01); *A61B 7/023* (2013.01)

(58) Field of Classification Search
None
See application file for complete search history.

(56) References Cited

U.S. PATENT DOCUMENTS

| | | | |
|---|---|---|---|
| 6,527,729 B1 | 5/2003 | Turcott | |
| 7,257,447 B2 | 8/2007 | Cates et al. | |
| 7,819,816 B2 | 10/2010 | Pu et al. | |
| 8,332,236 B2 | 12/2012 | Yurko et al. | |
| 2008/0273709 A1* | 11/2008 | Thiagarajan | A61B 7/04 381/67 |
| 2008/0275366 A1 | 11/2008 | Brohan et al. | |
| 2008/0294209 A1* | 11/2008 | Thompson | A61B 5/0031 607/3 |

(Continued)

FOREIGN PATENT DOCUMENTS

WO    2013101321 A1    4/2013

OTHER PUBLICATIONS

Corbishley et al., "Breathing Detection: Towards a Miniaturized, Wearable, Battery-Operated Monitoring System," IEEE Transactions on Biomedical Engineering, vol. 55, No. 1, 196-204 (Jan. 2008) 9 pp.

*Primary Examiner* — Sean P Dougherty
*Assistant Examiner* — Benjamin S Melhus
(74) *Attorney, Agent, or Firm* — Patterson Thuente Pedersen, P.A.

(57) ABSTRACT

Acoustic signals may be used to monitor one or more symptoms of a patient disease. A patient prescription may indicate one or more acoustic sensing programs that may be used to monitor at least on characteristic of an acoustic signal indicative of a patient symptom or disease. The patient prescription may also include a patient specific threshold. When the at least one characteristic of the acoustic signal is compared to the patient specific threshold an indication or warning signal may be generated. The warning signal may indicate a change in patient disease state.

28 Claims, 9 Drawing Sheets

(56) References Cited

U.S. PATENT DOCUMENTS

| | | | |
|---|---|---|---|
| 2008/0300651 A1* | 12/2008 | Gerber | A61B 5/0031 607/41 |
| 2010/0081942 A1* | 4/2010 | Huiku | A61B 5/02028 600/483 |
| 2010/0185109 A1 | 7/2010 | Zhang et al. | |
| 2012/0302898 A1 | 11/2012 | Zhang et al. | |
| 2013/0150754 A1 | 6/2013 | Rogers et al. | |
| 2013/0310726 A1 | 11/2013 | Miller et al. | |

\* cited by examiner

ACOUSTIC MONITORING TO DETECT MEDICAL CONDITION

This application claims the benefit of U.S. provisional application No. 62/067,817, filed on Oct. 23, 2014, the entire contents of which are incorporated by reference herein.

TECHNICAL FIELD

The disclosure is directed to acoustic sensing.

BACKGROUND

A wide variety of both external and implantable medical devices are available for delivering therapy and/or monitoring a physiological condition of a patient. For example, implantable medical devices (IMDs), such as cardiac pacemakers or implantable cardioverter defibrillators, provide therapeutic stimulation to the heart by delivering electrical therapy signals, such as pulses for pacing, or shocks for cardioversion or defibrillation. Other IMDs may, for example, provide electrical stimulation to other portions of the body, such as the gastro-intestinal track, brain, pelvic floor or spine. External medical devices may include, for example, ultrasound machines, fetal monitors, and insulin pumps. In some examples, one or more diagnostic or therapeutic decisions may be made based on signals monitored by one or more medical devices.

SUMMARY

In general, the disclosure is directed to system and methods that monitor one or more acoustic signals to detect a medical condition. In some examples, the acoustic signals may be used to track the status or progression of a patient disease state. In some examples, the manner in which the system monitors the one or more acoustic signals may be configured based on a patient prescription established by a caregiver.

In one example, the disclosure is directed to a method in including receiving a patient prescription; selecting between a plurality of acoustic sensing programs based upon the patient prescription, each of the plurality of acoustic sensing programs associated with detection of at least one characteristic of a sensed acoustic signal; setting at least one patient specific threshold for the at least one characteristic of the sensed acoustic signal based on the patient prescription, wherein the patient specific threshold corresponds to a change in patient state; operating a medical device according to the selected acoustic sensing program to sense an acoustic signal; and generating an indication based on a comparison of the at least one characteristic of the sensed acoustic signal and the patient specific threshold.

In another example, the disclosure is directed to medical device system including a telemetry module configured to receive a patient prescription; an acoustic sensor configured to sense an acoustic signal; and a processor configured to select between a plurality of acoustic sensing programs based upon the patient prescription, each of the plurality of acoustic sensing programs associated with detection of at least one characteristic of the sensed acoustic signal; set at least one patient specific threshold for the at least one characteristic of the sensed acoustic based on the patient prescription, wherein the patient specific threshold corresponds to a change in patient state; and generate an indication based on a comparison of the at least one characteristic of the sensed acoustic signal and the patient specific threshold.

In another example, the disclosure is directed to a system comprising means for receiving a patient prescription; means for selecting between a plurality of acoustic sensing programs based upon the patient prescription, each of the plurality of acoustic sensing programs associated with detection of at least one characteristic of a sensed acoustic signal; means for setting at least one patient specific threshold for the at least one characteristic of the sensed acoustic signal based on the patient prescription, wherein the patient specific threshold corresponds to a change in patient state; means for operating a medical device according to the selected acoustic sensing program to sense an acoustic signal; and means for generating an indication based on a comparison of the at least one characteristic of the sensed acoustic signal and the patient specific threshold.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
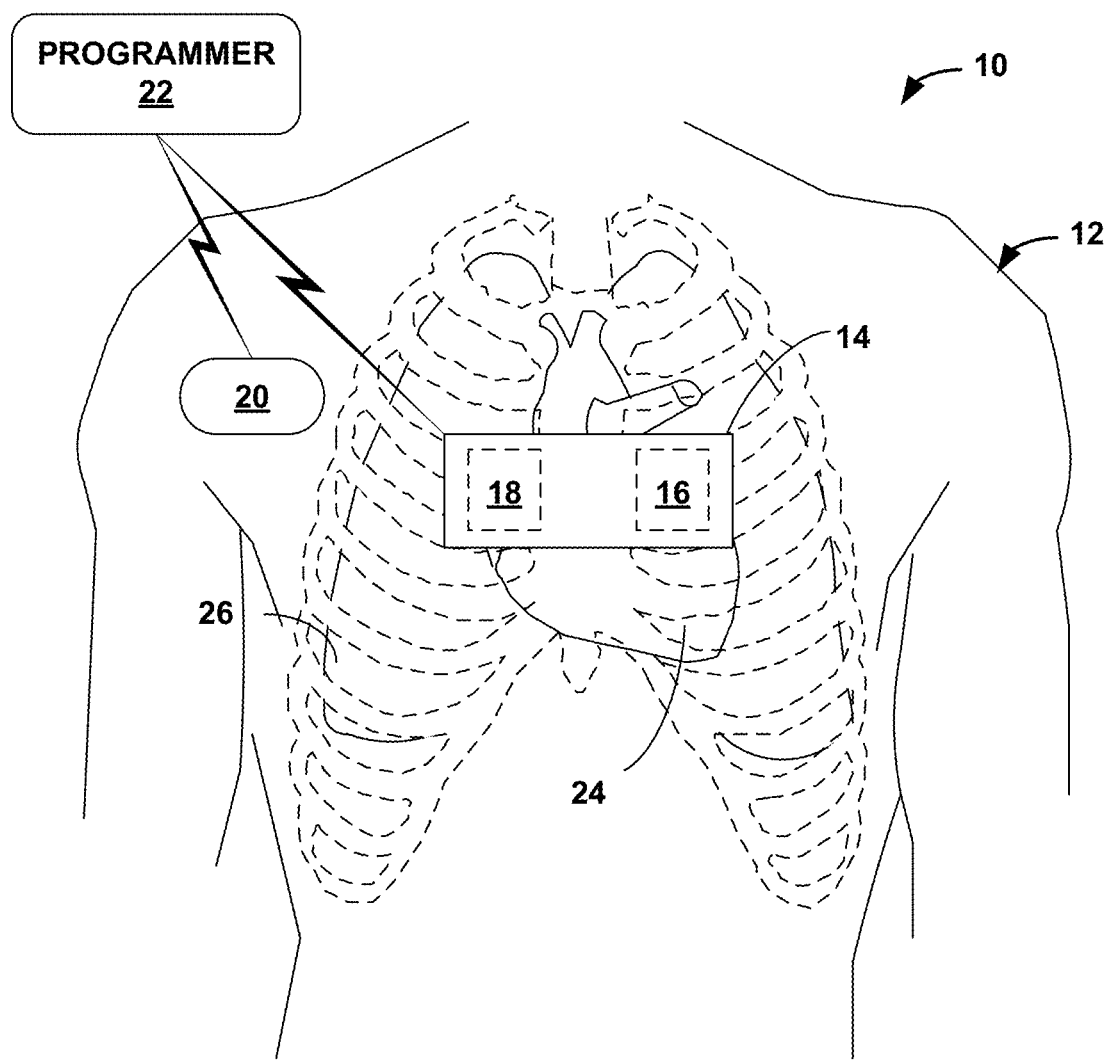
FIG. 1 conceptual diagram illustrating an exemplary system that monitors at least one acoustic signal in a patient.

The present disclosure describes example devices, systems, and method for programming an acoustic sensor and monitoring patient state based on a patient prescription. A medical device system consistent with the present disclosure may include one or more acoustic sensing devices which are programmed according to an acoustic sensing program. An acoustic sensing program may specify one or more of acoustic frequencies or frequency bands to be monitored, acoustic signal filtering instructions, acoustic signal templates, or detection thresholds, for example.

Each acoustic sensing program may be designed to monitor a single sound or acoustic signal-indicated symptom using the acoustic sensing device. For example, there may be plurality of acoustic sensing programs, each designed to detect a single sound or acoustic signal-indicated symptom. As an illustration, an acoustic sensing program could configure an acoustic sensing device to detect one or more individual, i.e., single, symptoms from respiration sounds, such as stridor, wheeze, crackles, rhonchi, Hamman's sign, pleural friction rub, fremitus, respiratory pattern, respiratory rate, or patient cough. In some examples, a plurality of acoustic sensing programs may be used together to monitor the progression of a patient's disease state. For example, in a patient at risk for progressive heart failure, a doctor may prescribe selection of a first acoustic sensing program for monitoring heart murmur, and a second acoustic program for monitoring lung crackles. In some examples, each of the programs may monitor different characteristics of the same acoustic signal. The programs, when implemented together by an acoustic sensing device, may be provide multiple indications of the patient's disease state from the perspective of different physiological conditions that both relate to heart failure.

A patient prescription may include information regarding which acoustic sensing programs should be selected based on the disease state of the patient. For example, a combination of sensing programs may be selected based on a patient prescription that is disease specific. For example, the programs included in a patient prescription for a patient with heart failure are different than for a patient with asthma. The patient prescription may include one or more indication thresholds. For example, the patient prescription may include an indication threshold for each of the acoustic signals being monitored or for each characteristic of an acoustic signal being monitored, as well as an indication based on a combination of the monitored acoustic signals or characteristics. The indication threshold based on a combination may include thresholds for each of the acoustic signals or characteristics being monitored, but at different levels than each acoustic signal or characteristic indication individually. In some examples, the patient prescription may include a plurality of indication thresholds that may be used to track the progression of the patient's symptoms. In some examples, at least one of the indication thresholds is patient specific.

In some examples, a warning signal is sent to a either the patient or a physician based on the indication. The warning signal may be sent from a sensing device over a network to a remote network device, such as an external server or computing device. In some examples, the physician may modify the patient prescription for acoustic sensing by the sensing device based on a received warning signal. In some examples, modified patient prescription may be transmitted from remoted device to the sensing device or another medical device.

FIG. 1 is a conceptual diagram illustrating an exemplary system 10 that detects at least one acoustic signal in patient 12. In particular, system 10 includes an external device such as an external patch 14, an IMD 20, and a programmer 22. Although shown with both external patch 14 and IMD 20, in various examples system 10 may include only one of an external device such as external patch 14 or IMD 20. External patch 14 may include a flexible pad with an adhesive backing. In some examples, the adhesive may be reusable. Other example external devices may include, for example, an external device including an acoustic sensor which is held in place with a belt or harness. As shown in FIG. 1 external patch 14 may be placed on patient 12 over the patient's chest. In some examples the external patch 14 is located over heart 24. This placement allows for acoustic sensor 16 to pick up heart sounds, including, for example, the sound of the aortic valve and/or pulmonary valve closing. In some examples, acoustic sensor 16 may detect a signal including heart sounds S1, S2, S3, and S4. In some examples, external patch 14 is placed so that the acoustic sensor 16 is located over spaces between the ribs. Placement between the ribs may allow for better capture of heart sounds. In some examples, the optimal location for acoustic sensor 16 may be determined by referencing a chest X-ray for the patient 12. In some examples, not shown, external patch may include two or more acoustic sensors or more than one external patch may be used. In examples where external patch 14 includes two acoustic sensors, the patch may be located in a manner so that one acoustic sensor is located to capture the closing of the aortic value and the other acoustic sensor located to capture the pulmonary valve closing. In addition to heart sounds S1-S4, external patch 14 may be configured to detect heart-based sounds including heart murmur, pulse, gallop rhythm, or pericardial friction rub.

In some examples, external patch 14 may be located over the chest and lungs 26 of patient 12 in order to pick up one or more respiratory sounds, alone or in combination with heart-based sounds, including, for example, stridor, wheeze, crackles, rhonchi, Hamman's sign, pleural friction rub, fremitus, bronchophonyathma, respiratory pattern, respiratory rate, or cough. The location may be determined, at least in part, based on the sounds to be picked up by external patch 14. In other examples, external patch 14 may be located at other positions on the body of patient 12, not shown, in order to pick up other body sounds. For example, external patch 14 may be located to pick up gastrointestinal sounds including, for example, stomach rumbles, growling, gurgling, or borborygmus. Other sounds which may be monitored by external patch 14 include fetal sounds such as fetal heart rate, urinary voiding sounds for lower urinary tract symptoms, and vascular sounds indicative of intracranial vascular lesions, blood obstruction, stenosis, aneurysm, arteriovenous, malformation, or a fistula, for example.

System 10 also includes a programmer 22. External patch 14 is communicatively coupled to programmer 22. In some examples, programmer 22 takes the form of a handheld computing device, computer workstation, or networked computing device that includes a user interface for presenting information to and receiving input from a user. A user, such as a physician, technician, surgeon, electro-physiologist, or other clinician, may interact with programmer 22 to program external patch to monitor and analyze specific acoustic signals based on a patient prescription. In some examples the user may also interact with programmer 22 to retrieve physiological or diagnostic information from external patch 14. For example, programmer 22 may receive an acoustic signal from external patch 14 for analysis. In other examples, programmer 22 may receive an alert signal when one or more parameters of a monitored acoustic signal exceed a predetermined threshold. In some examples, the functions of programmer 22 may be split between a processor within programmer 22 and an internal processor within external patch 14.

External patch 14 and programmer 22 and/or IMD 20 and programmer 22 may communicate via wireless communication using any techniques known in the art. Examples of communication techniques may include, for example, low frequency or radiofrequency (RF) telemetry. Other techniques are also contemplated. In some examples, programmer 22 may include a programming head that may be placed proximately to the patient's body near the IMD 20 implant site in order to improve the quality or security of communication between IMD 20 and programmer 22. In other examples, programmer 22 may be located remotely from IMD 20 or external patch 14, and communicate with IMD 20 and/or external patch 14 via a network. In some examples, IMD 20, external patch 14, and programmer 22 may work with general network technology and functionality similar to that provided by the Medtronic CareLink® Network developed by Medtronic, Inc., of Minneapolis, Minn.

In some examples, programmer 22 may process one or more acoustic signals received from either external patch 14 or IMD 20 to determine if a change in patient state has occurred. In some examples, acoustic signals may be monitored only with external patch 14 or only with IMD 20. For example, programmer 22 may compare one or more features of the received acoustic signal(s) to a predetermined threshold. In some examples, the threshold may be set based on a patient specific prescription.

In some examples, system 10 includes an IMD 20. In some examples, IMD 20 is used to detect one or more acoustic signals while implanted within patient 12. The location of IMD 20 within patient 12 may be selected based on a patient prescription defined by a physician or other caregiver. For example, IMD 20 may be implanted near the heart 24 if the patient prescription requires detection of heart sounds. In examples where the prescription requires monitoring of respiratory sounds, IMD 20 may be placed proximate to lungs 26. In examples where the prescription requires monitoring gastrointestinal sounds, IMD 20 may be implanted close to the patient's digestive tract (not shown). In some examples, IMD 20 may be implanted in a generic location within patient 12 and be in communication with leadless sensors implanted proximate to the area of interest. In some examples, IMD 20 may include electrodes for the delivery of stimulation therapy to patient 12. In some examples, IMD 20 may include a plurality of acoustic sensors and/or electrodes. The housing electrodes may be formed integrally with an outer surface of a hermetically sealed housing of the IMD, or otherwise be coupled to the housing. The housing electrodes may be defined by uninsulated portions of a portion, e.g., an outward facing portion of the housing of IMD 20.

In some examples, programmer 22 may receive acoustic signals detected by both external patch 14 and IMD 20. For example, external patch 14 may be located proximate to a first location selected based on a patient prescription and programmed based on a first acoustic sensing program to detect a first acoustic signal indicative of a first patient symptom associated with a patient condition. IMD 20 may be located proximate to a second location selected based on the patient prescription and programmed based on a second acoustic sensing program to detect a second acoustic signal indicative of a second patient symptom associated with the patient condition. In some examples, the sensed acoustic signals from both the external patch 14 and IMD 20 may be provided to programmer 22 for processing. In some examples, programmer 22 compares the first acoustic signal to a first threshold selected based on the patient prescription and the second acoustic signal to a second threshold selected based on the patient prescription. In other examples, programmer 22 compares a first characteristic of an acoustic signal to the first threshold selected based on the patient prescription and a second characteristic of the acoustic signal to the second threshold based on the patient prescription. In some examples, programmer 22 may generate an alert or warning signal based on one or both of the comparisons.

Figure 2:
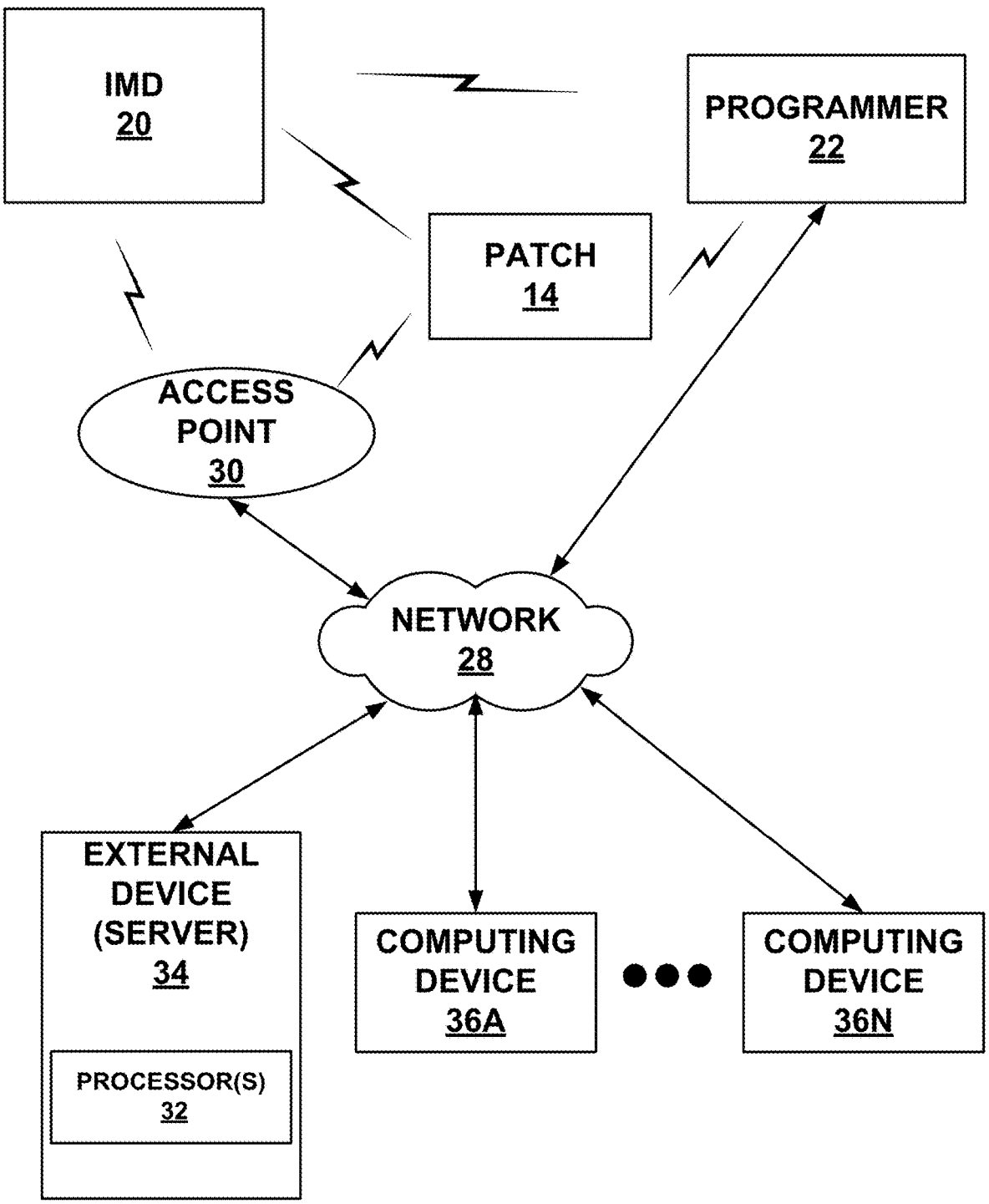
FIG. 2 is a conceptual block diagram illustrating an example system that includes an external device and one or more computing devices that are coupled to an external device, an IMD and/or a programmer (as shown in FIG. 1) via a network.

FIG. 2 is a conceptual block diagram illustrating an example system that includes an external device, such as server 34, and one or more computing devices 36A-36N that are coupled to an external device such as external patch 14, IMD 20 and programmer 22 shown in FIG. 1 via a network 28. Network 28 may be generally used to transmit diagnostic information (e.g., an indication an acoustic signal has exceeded a threshold) from programmer 22 to a remote external computing device. Although shown with both an external device such as external patch 14 and IMD 20, the system may include only one or the other of external patch 14 or IMD 20. In some examples, the acoustic signals such as heart sounds signals and/or lung sounds signals may be transmitted to an external device for processing. In some examples, information transmitted by external patch 14 and/or IMD 20 may allow a clinician or other healthcare professional to monitor patient 12 remotely. In some examples, external patch 14 may use its telemetry module 18 (discussed in more detail below with respect to FIG. 4) to communicate with programmer 22 via a first wireless connection, and to communicate with an access point 30 via a second wireless connection, e.g., at different times. In the example of FIG. 2, access point 30, programmer 22, IMD 20, server 34, and computing devices 36A-36N are interconnected, and able to communicate with each other, through network 28. In some cases one or more of access point 30, programmer 22, server 34, and computing devices 36A-36N may be coupled to network 28 via one or more wireless connections. External patch 14, IMD 20, programmer 22, server 34 and computing devices 36A-36N may each comprise one or more processors, such as one or more microprocessors, DSPs, ASICs, FPGAs, programmable logic circuitry, or the like, that may perform various functions and operations, such as those described herein.

Access point 30 may comprise a device that connects to network 28 via any of a variety of connections, such as telephone dial-up, digital subscriber line (DSL), cellular wireless, or cable modem connections. In other examples, access point 30 may be coupled to network 28 through different forms of connections, including wired or wireless connections. In some examples, access point 30 may be co-located with patient 12 and may comprise one or more programming units and/or computing devices (e.g., one or more monitoring units) that may perform various functions and operations described herein. For example, access point 30 may include a home-monitoring unit that is co-located with patient 12 and that may monitor the activity of external patch 14 and IMD 20. In some examples, server 34 or computing devices 36 may control or perform any of the various functions or operations described herein, e.g., determine, based on acoustic signal, whether a warning signals should issue based on whether one or more predetermined thresholds has been met. Server 34 may receive one or more acoustic signals from either external patch 14, IMD 20, or both.

In some cases, server 34 may be configured to provide a secure storage site for archival of diagnostic information (e.g., occurrence of an acoustic signal meeting or exceeding a predetermined threshold and attendant circumstances such as patient posture and activity level) that has been collected and generated from external patch 14, IMD 20 and/or programmer 22. Network 28 may comprise a local area network, wide area network, or global network, such as the Internet. In some cases, programmer 24 or server 34 may assemble pulmonary hypertension and heart failure information in web pages or other documents for viewing by trained professionals, such as clinicians, via viewing terminals associated with computing devices 36. The system of FIG. 2 may be implemented, in some aspects, with general network technology and functionality similar to that provided by the Medtronic CareLink® Network developed by Medtronic, Inc., of Minneapolis, Minn.

In the example of FIG. 2, external server 34 may receive information regarding a first acoustic signal from external patch 14 and information regarding a second acoustic signal from IMD 20 via network 28. Based on the acoustic signal information received, processor(s) 32 may preform one or more of the functions described herein with respect to signal analyzer 46 and processor 44 (described with respect to FIG. 3, below). In some examples, acoustic signals are transmitted to an external device and the external device, such as server 34, processes the signals to determine if a patient state has changed. In some examples, a change in patient state may be determined based on a comparison of one or more characteristics of the acoustic signal to a threshold.

Figure 3:
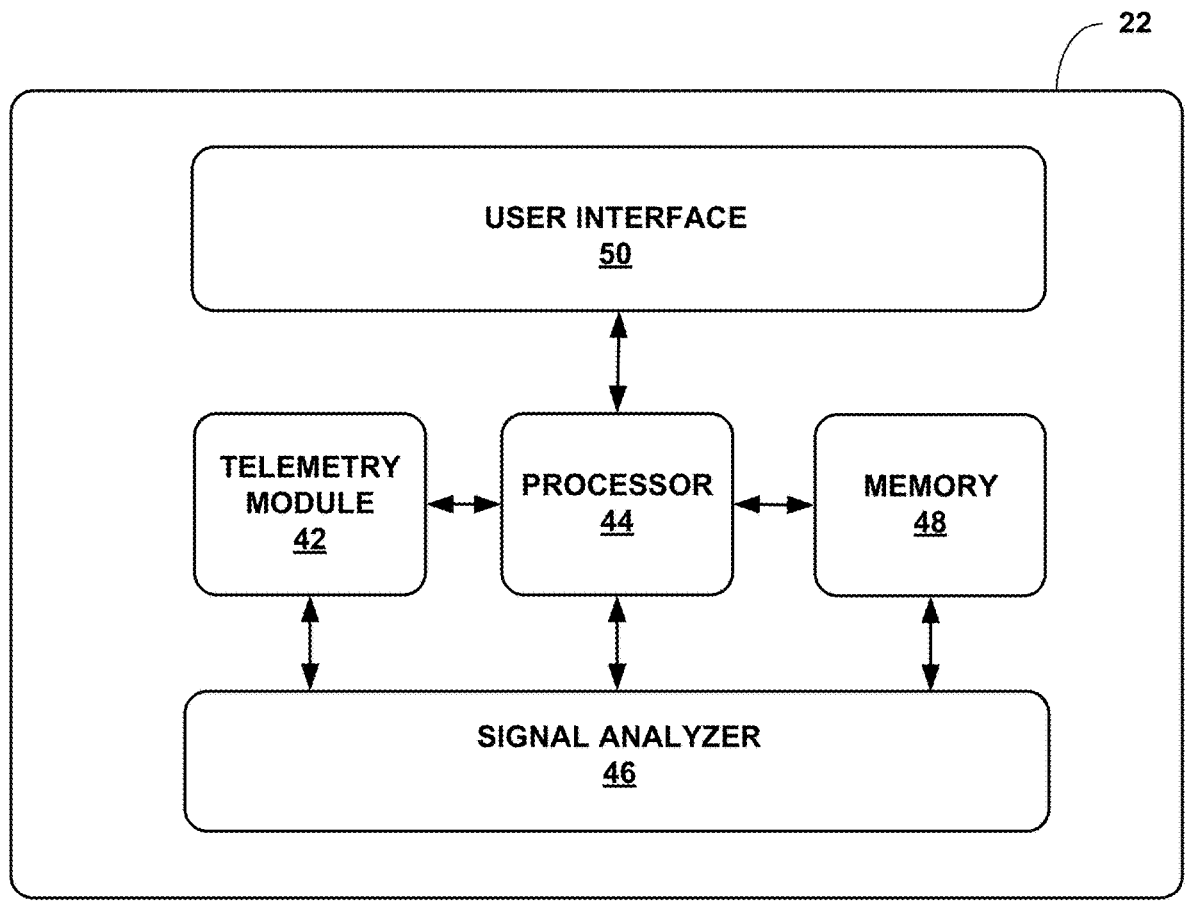
FIG. 3 is a functional block diagram illustrating an example programmer for programming an external device and/or an IMD.

FIG. 3 is a functional block diagram illustrating an example programmer 22 for programming external patch 14 and/or IMD 20. IN some examples, a separate programmer may be used for each of external patch 14 and IMD 20. Programmer 22 may be provided in the form of a handheld device, portable computer or workstation that provides a user interface to a physician or patient. In the example of FIG. 3, programmer 22 includes processor 44, memory 48, telemetry interface 42, user interface 50, and signal analyzer 46. In general, a user, i.e., a physician or clinician uses programmer 22 to program and control IMD 20 and/or external patch 14. In addition, programmer 22 may be used to determine if a patient state has changed based on information collected by external patch 14 and/or IMD 20. The patient state being monitored may be selected by a user via user interface 50. The patient state may be selected based on a patient prescription.

In the example of FIG. 3, a user interacts with processor 44 via user interface 50 in order access diagnostic and program information regarding patient 12 stored in memory 48. The user may also interact with processor 44 via user interface 50 in order to modify program settings for external patch 14 and/or IMD 20. User interface 50 may be a graphical user interface (GUI). The user interface 50 may also include one or more input media. In put media may include, for example, a keyboard or a touchscreen. In addition, the user interface may include lights, audible alerts, or tactile alerts. Processor 44 may include a microprocessor, a microcontroller, a DSP, an ASIC, an FPGA, or other equivalent discrete or integrated logic circuitry.

In some examples, processor 44 may control external patch 14 and/or IMD 20 via telemetry module 42. For example, processor 44 may be used to determine when external patch 14 collects acoustic signals from acoustic sensor 18. Processor 44 may also modify one or more therapy parameters used to delivery therapy by IMD 20 in response to heart sound signals collected by external patch 14. In particular, processor 44 may transmit program signals to external patch 14 or IMD 20 via telemetry module 42. In some examples, external patch 14 may simply include an acoustic sensor 18 and transmit the sensed signal to programmer 22 for analysis.

Signal analyzer 46 receives an electrical signal that was generated by acoustic sensor 18 and transmitted via telemetry module 52 of external patch 14 to telemetry module 42. In one example, signal analyzer 46 may process the sensor signals generated by acoustic sensor 18 to detect an acoustic signal characteristic selected based on a patient prescription. Signal analyzer 46 may also generate one or more acoustic metrics indicative of a particular patient state based on the characteristics of one or more of the detected acoustic signals. For example, when the acoustic signal is a heart sound signal, signal analyzer 46 may determine the amplitude of heart sounds A2 (systemic blood pressure) and P2 (pulmonary blood pressure). Signal analyzer 46 may generate an envelope signal and apply an algorithm that uses an adaptively decaying threshold, to detect events within the envelope signal. An event may be, for example, a change in the signal being monitored. The event may be detected based on one or more characteristics of the signal crossing a threshold. For example, a signal amplitude, rate, or number of occurrences within a predetermined time period, may be compared to the threshold. Signal analyzer 46 extracts event features from the detected events, and determines one or more parameters based on the features. In some examples, signal analyzer 46 may process the signal from acoustic sensor 18 of external patch 14 in order to extract features of a first acoustic signal and process a signal from acoustic sensor 60 of IMD 20 in order to extract features of a second acoustic signal.

Signal analyzer 46 may provide an indication of a determination of a change in patient state to processor 44. In some examples, signal analyzer 46 may provide an indication of one ore more acoustic signal parameters derived from the signals received from external patch 14 and IMD 20. The operation of signal analyzer in according with these example methods if described in greater detail below with respect to FIGS. 6-8. In any case, an acoustic signal based indication of patient status or change in patient status may be output to processor 44, which may allow, modify or withhold delivery of therapy based on the patient status. In some examples, programmer 22 may send an indication of the patient status a clinician or physician over network 28. Processor 44 or signal analyzer 46 may store the acoustic signal parameters in memory 48. In some examples, processor 44 may store the determination of patient status along with any changes made to therapy based on the patient status in memory 48.

Although processor 44 and signal analyzer 46 are illustrated as separate module in FIG. 3, processor 44 and signal analyzer 46 may be incorporated in a single processing unit. Signal analyzer 46 may be a component of or a module executed by processor 44. Furthermore, the components of and functionality provided by signal analyzer 46 are described herein with respect to examples in which signal analyzer 46 is located within programmer 24. However, it is understood, and discussed in more detail below, that any one or more signal analyzers 46 may be individually or collectively provided by any one or more devices, such as IMD 20, external patch 14, or server 34, to individually or collectively provide the functionality described herein.

Memory 48 includes computer-readable instructions that, when executed by processor 44, cause programmer 22 to perform various functions attributed to programmer 22 and processor 44 herein. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 48 may also store one or more therapy programs or parameters to be executed by IMD 20. Memory 48 may also store instructions regarding when external patch 14 collects heart sound signals.

Telemetry module 42 includes any suitable hardware, firmware, software or any combination thereof for communicating with another device, such as external patch 14 (FIG. 1). Under the control of processor 44, telemetry module 42 may send downlink telemetry to and receive uplink telemetry from external patch 14 and/or IMD 20 with the aid of an antenna, which may be internal and/or external. Information which processor 44 may transmit to IMD 20 via telemetry module 42 may include an indication of a change in patient state or a change in programming to change one or more therapy parameters. The indication may be based acoustic signals.

Figure 4:
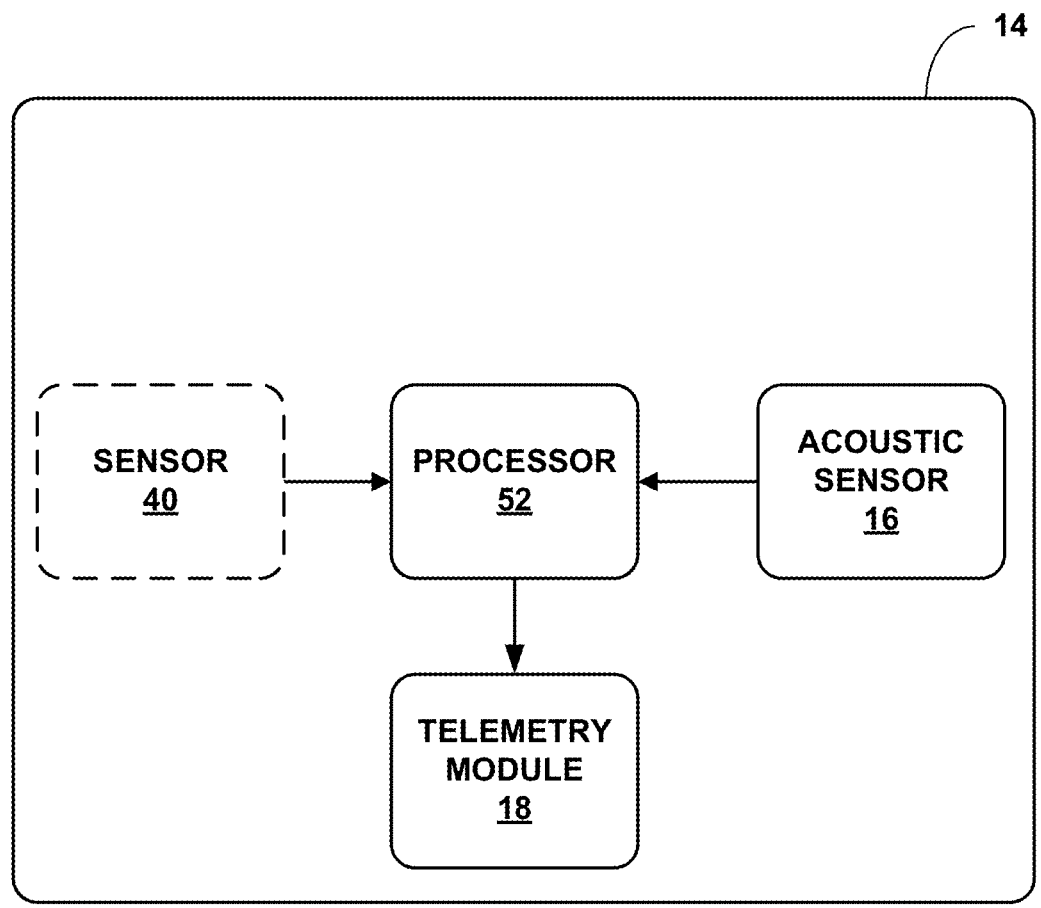
FIG. 4 is a functional block diagram illustrating an example external device including an acoustic sensor.

FIG. 4 is a functional block diagram illustrating an example external patch 14. External patch 14 includes acoustic sensor 16, telemetry module 18, and processor 52. In some examples, external patch 14 may include one or more additional sensors 40. External patch 14 also includes a power source, such as a rechargeable or non-rechargeable battery, not shown. External patch 14 may include a reusable adhesive. The adhesive may be used to hold external patch 14 in place on patient 12 as shown in FIG. 1. In some examples, external patch 14 is located on patient 12 so that acoustic sensor 16 is located approximately above an area of interest. For example, in instances where a patient prescription includes monitoring one or more heart sounds, external patch 14 may be located so that acoustic sensor 16 may be located approximately above one of the valves of heart 24. In some examples, acoustic sensor 16 may be located between two ribs of patient 12 over lungs 26 in order to pick up respiratory sounds.

Acoustic sensor 16 generates an electrical signal based on sound or vibration, e.g., sensed heart sounds of patient 12, and may be implemented as a piezoelectric sensor, a microphone (a transducer or sensor using electromagnetic induction, capacitance change or piezoelectricity), an accelerometer, or other type of acoustical sensor. In some examples, acoustic sensor 18 may comprise one or more sensors. For example, acoustic sensor 16 may include multiple accelerometer devices. Information obtained from acoustic sensor 16 may be used to aid in the detection of a change in patient state. For example, in instances where the patient prescription calls for monitoring heart sounds, the information obtained from acoustic sensor 16 may aid in the detection of the progression of pulmonary hypertension or heart failure. The signal from acoustic sensor 16 may be processed by processor 52 before being transmitted to external programmer 22 or IMD 20 via telemetry module 18. In some examples, a warning signal indicating a change in patient state may be transmitted to external programmer 22 or IMD 20 via telemetry module 18.

In some examples, external patch 14 may include one or more additional sensors 40. Additional sensor 40 may be one or more of an additional acoustic sensor, a temperature sensor, electrodes, or an activity level or posture sensor, for example. The signal from additional sensor 40 may be processed by processor 52 before being transmitted to external programmer 22 or IMD 20. In some examples, a warning signal indicating a change in patient state may be transmitted to external programmer 22 or IMD 20 via telemetry module 18.

In some examples, processor 52 filters acoustic signals from acoustic sensor 16 and additional sensor 40 at different frequencies. The location different between the two sensors may be used to help differential between various features of the acoustic signal. For example, the respective locations of acoustic sensor 16 and additional sensor 40 may help differentiate between various heart sounds, such as the A2 and P2 heart sounds.

In some examples, acoustic sensor 16 and additional sensor 40 may detect an acoustic waveform including more than one sound signal. For example, when external patch 14 is placed over heart 24, the acoustic signal may include both heart sounds and lung sounds. Processor 52 may amplify the signals from acoustic sensor 16 and additional sensor 40 prior to transmission via telemetry module 18. In some examples, processor 52 may use band-pass filters to separate two or more acoustic signals collected by acoustic sensor 16 and/or additional sensor 40. For example, two band-pass filters may be used to separate heart sound signals from lung sound signals. In some examples, the acoustic waveform is transmitted to programmer 22 via telemetry module 18 for processing. Processor 44 of programmer 22 may use one or more band-pass filters to separate various acoustic signals collected by external patch 14. In some examples, processor 52 may perform a portion of the signal processing with the other portion of the signal processing performed by processor 44 of programmer 22. For example, processor 52 may separate two ore more acoustic signals from different areas of interest within patient 12, while processor 44 detects individual characteristics of the separated signals. Based on the characteristics, processor 44 may determine if there has been a change in patient state.

Figure 5:
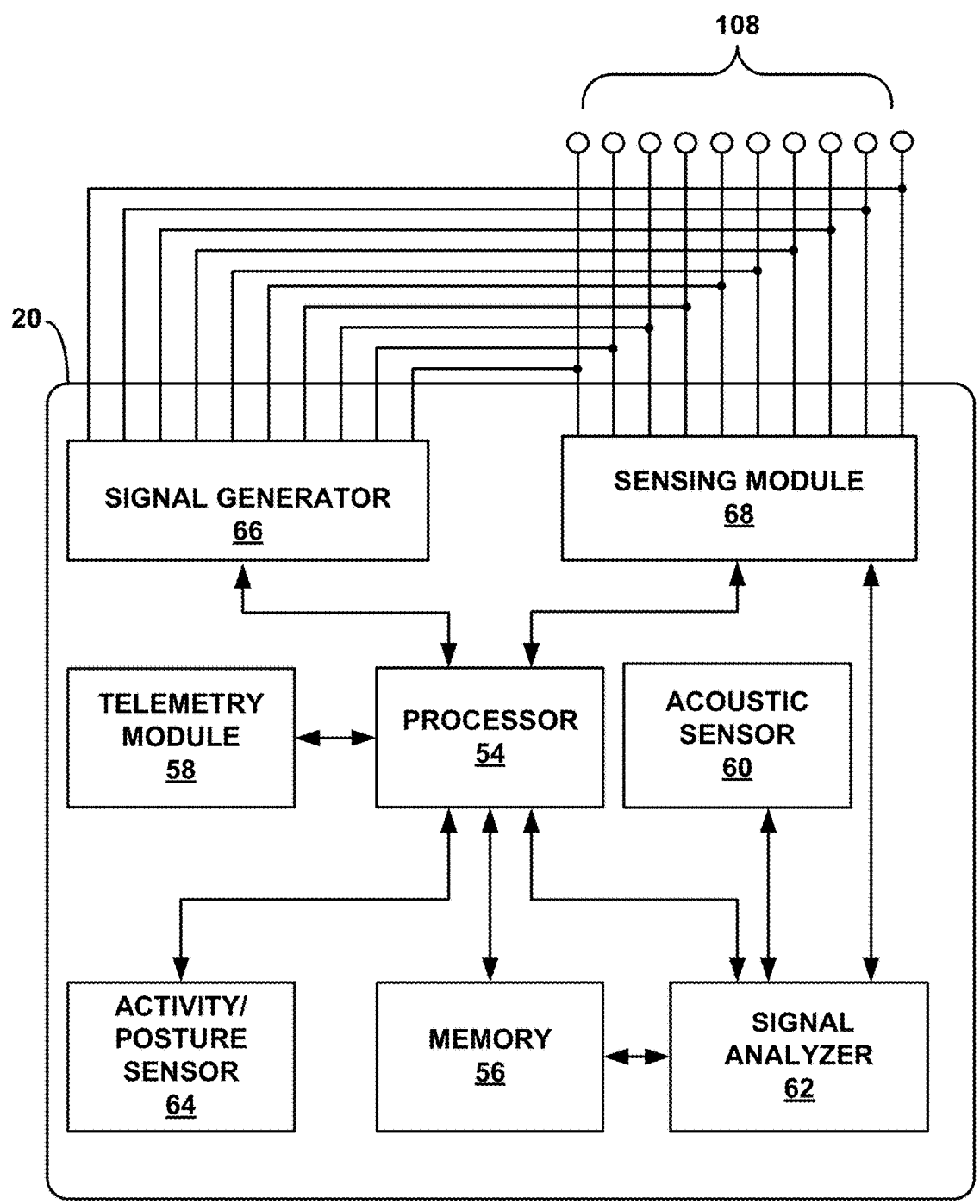
FIG. 5 is a functional block diagram of an example IMD including an acoustic sensor.

FIG. 5 is a functional block diagram of an example IMD 20. IMD 20 may include a processor 54, a memory 56, a telemetry module 48, acoustic sensor 60, a signal analyzer 62 an activity/posture sensor 64, a signal generator 66 and a sensing module 68. Memory 56 includes computer-readable instructions that, when executed by processor 54, cause IMD 20 and processor 56 to perform various functions attributed to IMD 20 and processor 54 herein. Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 54 may include any one or more of a microprocessor, a controller, a digital signal processor (DSP), an application specific integrated circuit (ASIC), a field-programmable gate array (FPGA), or equivalent discrete or analog logic circuitry. In some examples, processor 54 may include multiple components, such as any combination of one or more microprocessors, one or more controllers, one or more DSPs, one or more ASICs, or one or more FPGAs, as well as other discrete or integrated logic circuitry. The functions attributed to processor 54 herein may be embodied as software, firmware, hardware or any combination thereof. Generally, processor 54 controls signal generator 66 to deliver electrical stimulation therapy to a target location of patient 12 according to a selected one or more of therapy programs or parameters, which may be stored in memory 56. As an example, processor 54 may control signal generator 66 to deliver electrical stimulation pulses with the amplitudes, pulse widths, frequency, or electrode polarities specified by the selected one or more therapy programs or parameters.

Signal generator 66 is configured to generate and deliver electrical stimulation therapy to patient 12. As shown in FIG. 5, signal generator 66 is electrically coupled to electrodes 108, e.g., via conductors. In some examples, not shown in FIG. 2, IMD 20 may connect to one more leads. In some examples, one or more electrodes 108 may be on the housing of IMD 26. For example, when the target location is heart 24, the signal generator 66 may deliver pacing, defibrillation or cardioversion pulses to heart 24 via at least two of electrodes 108. In other examples, the target location may be one of the phrenic nerve, the spinal cord, the brain, the gastrointestinal tract, the pelvic floor, or the urethral or anal sphincter. In some examples, signal generator 66 delivers stimulation in the form of signals other than pulses such as sine waves, square waves, or other substantially continuous time signals.

Signal generator 66 may include a switch module (not shown) and processor 54 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 68 monitors electrical signals from any combination of electrode 108. Sensing module 68 may also include a switch module which processor 54 controls to select which of the available electrodes are used to sense electrical activity from the target location, depending upon which electrode combination is used in the current sensing configuration.

Sensing module 68 may include one or more detection channels, each of which may comprise an amplifier. The detection channels may be used to sense electrical signals from the target location. For example, the electrical signals may be cardiac signals. Some detection channels may detect events, such as R-waves or P-waves, and provide indications of the occurrences of such events to processor 54. One or more other detection channels may provide the signals to an analog-to-digital converter, for conversion into a digital signal for processing or analysis by processor 54.

For example, sensing module 68 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 54 then uses that detection in measuring frequencies of the sensed events.

IMD 20 also includes acoustic sensor 60, signal analyzer 62 and activity sensor 64. Acoustic sensor 60 generates an electrical signal based on sound or vibration, e.g., sensed heart sounds of patient 12, and may be implemented as a piezoelectric sensor, a microphone, an accelerometer, or other type of acoustical sensor. In some examples, acoustic sensor 60 may comprise more than one sensor. For example, acoustic sensor 60 may include multiple accelerometer or piezoelectric devices. Activity/posture sensor 64 may also comprise one or more accelerometers. Information obtained from acoustic sensor 60 and activity sensor 64 may be used to provide an indication that a patient state has changed. In some examples, signals from the sound sensor 60 and activity sensor 64 are provided to signal analyzer 62 and, based on information extracted from the signals, and one or more thresholds set based on a patient prescription, an indication of a change in patient state may be generated.

For example, a normal resting heart rate for adults ranges from 60 to 100 beats a minute. An unusually high or low heart rate may indicate an underlying problem, e.g. consistently above 100 beats a minute (tachycardia) or below 60 beats a minute (bradycardia), especially accompanied with other signs or symptoms, such as fainting, dizziness or shortness of breath. In some examples, a first threshold may be set at approximately 60 beats a minute. If the heart rate falls below the first threshold, an indication may be generated. A second threshold may be set at approximately 100 beats a minute. If the heart rate goes above the second threshold, an indication may be generated.

In other examples, changes in features and intervals of bowel sound may be detected according to a pathological condition. For example, compared with healthy volunteers, patients with mechanical obstruction have the regular occurrence of clustered bowel sounds, defined as 3-10 regular sounds, occurring once every five seconds, preceded and followed by at least one minute of silence. Accordingly, a threshold may be set at approximately 3 consecutive bowels sounds. An indication may be generated if more than 3 loud, gurgling rushed bowels sounds occur within a predetermined amount of time indicating a possible mechanical obstruction.

In another example, in the diabetes mellitus patients, the sum of the amplitude of the gastroduodenal sound was significantly lower after food intake than in healthy adults e.g. soft, low, widely separated sounds (such as one or two occurring in two minutes) or sounds not heard for 3-5 minutes. In one example, the sum of the amplitude of GI sound is approximately $1 \times 10^5$ mV/15 min for patients with diabetes mellitus compared to approximately $12 \times 10^5$ mV/15 min in a healthy individual. In some examples, the sum of the amplitude of GI sound in a healthy individual is approximately 10 times that of an individual with GI motility problems. Accordingly, a threshold may be set somewhere between approximately $1 \times 10^5$ mV/15 min and $10 \times 10^5$ mV/15 min. If the amplitude of the gastroduodenal sound is below the threshold, an indication may be generating indicating the possibility of hypoactive bowel or diabetes mellitus.

In another example, void sound measures the volume of urine released from the body, the speed with which it is released, and how long the release takes. Normal values vary depending on age and sex. For example, at ages 66-80, an average flow rate for males is 9 ml/sec and for females is 19 ml/sec, which will be converted to sound amplitude based on the standard curve. The increase in sound amplitude (urine flow) may indicate weak urethral muscle or urinary incontinence. If there is a bladder outlet obstruction (e.g. BPH) or if the bladder muscle is weak, a decrease in urine flow or interruptions can be measured with sound. Thresholds may be set to indicate an increase in urine flow indicating weak urethral muscle or urinary incontinence. For example, a threshold may be set at approximately 10 percent above a patient's normal urine flow. If the urine flow crosses the threshold, an indication may be generated indicating that the patient's urethral muscle may be weakening or the patient may be experiencing urinary incontinence.

In another example, a threshold may be set for fetal heart sounds. A baby's heart beat start at about 5 weeks gestation about 80-85 beats per minute (BPM). It increases its rate about 3 beats per minute per day during that first month. By the beginning of the 9th week of pregnancy, the normal fetal heart rate is an average of 175 BPM. At this point it begins a rapid deceleration to the normal fetal heart rate for the middle of the pregnancy of about 120-180 BPM. In some examples, a threshold which changes overtime may be used to monitor a baby's heart rate. If the heart rate falls below the threshold, an indication may be generated indicating the baby may be in distress.

In the illustrated example of FIG. 5, acoustic sensor 60 is enclosed within the housing of IMD 20. In other examples, acoustic sensor 60 may be located on a lead that is coupled to IMD 20 or may be implemented in a remote sensor that wirelessly communicates with IMD 20. In any case, acoustic sensor 60 is electrically or wirelessly coupled to circuitry contained within IMD 20.

Using a remote sensor or a sensor on a lead for acoustic sensor 60 allows for a single IMD 20 to be used to detect a variety of different acoustic signals. For example, the implant location of IMD 20 may be substantially the same regardless of where a target location for acoustic signals is located. The location of the lead or remote sensor may be determined based on a patient prescription detailing which acoustic signal is to be monitored by IMD 20.

Signal analyzer 62 receives the electrical signal generated by acoustic sensor 60. Signal analyzer 62 may be programmed to process the electrical signal generated by acoustic sensor 60 based on a patient prescription. In one example, signal analyzer 62 may process the sensor signal generated by acoustic sensor 60 to detect lung sounds and respiratory characteristics such as inspiration, expiration, respiratory rate, depth of inspiration, and/or the presence of a cough or other respiratory anomalies such as rales, rhonchi, stridor or wheezing. In other examples, signal analyzer 62 may programmed to detect one of vascular sounds, cardiac sounds, gastrointestinal sounds, fetal sounds or voiding sounds. In some examples, signal analyzer 62 may also receive electrical signals generated by acoustic sensor 16 of external patch 14. Signal analyzer 62 may process both the acoustic signals from the acoustic sensor 16 of external patch 14 and the acoustic sensor 60 of IMD 20. Signal analyzer 62 may process the signals to determine whether a change in patient state has occurred or whether one or more symptoms are present in patient 12 as discussed below with respect to FIGS. 6-8.

Although processor 54 and signal analyzer 62 are illustrated as separate modules in FIG. 5, processor 54 and signal analyzer 62 may be incorporated in a single processing unit. Signal analyzer 62, and any of its components, may be a component of or a module executed by processor 54.

Furthermore, the components of and functionality provided by signal analyzer 62 are described herein with respect to examples in which signal analyzer 62 is located within IMD 20. However, it is understood that any one or more signal analyzers 62 may be individually or collectively provided by any one or more devices, such as IMD 20 and programmer 22, to individually or collectively provide the functionality described herein. Programmer 22 may receive electrical signals generated by acoustic sensor 60 from IMD 20 in examples in which programmer 22 includes signal analyzer 46.

As illustrated in FIG. 5, IMD 20 may also include an activity and/or posture sensor 64. Activity and/or posture sensor 64 may, for example, take the form of one or more accelerometers, tension sensor, force sensor, dislocation sensor, or any other sensor known in the art for detecting activity, e.g., body movements or footfalls, or posture. In some examples, activity and/or posture sensor 64 may comprise a three-axis accelerometer. In some examples, acoustic sensor 60 and activity and/or posture sensor 64 may comprise one or more common accelerometers. As will be described in greater detail below with reference to FIGS. 6-8, processor 54 or signal analyzer 62 may use signals from activity and/or posture sensor 64 in various aspects of the acoustic signal analysis. For example, processor 54 may direct acoustic sensors 16 to collect acoustic signals during periods in which the activity level of patient 12 is below a predetermined threshold.

Telemetry module 58 includes any suitable hardware, firmware, software or any combination thereof for communicating with another device, such as programmer 22 or external patch 14 (FIG. 1). Under the control of processor 54, telemetry module 58 may receive downlink telemetry from and send uplink telemetry to programmer 24 with the aid of an antenna, which may be internal and/or external. In some examples, processor 54 may transmit directions to external patch 16 and receive acoustic signals for processing by processor 54 or signal analyzer 62. Processor 54 may also transmit signals, e.g., ECG or ECG signals, produced by sensing module 68 and/or signals by acoustic sensor 60 to programmer 22.

Figure 6:
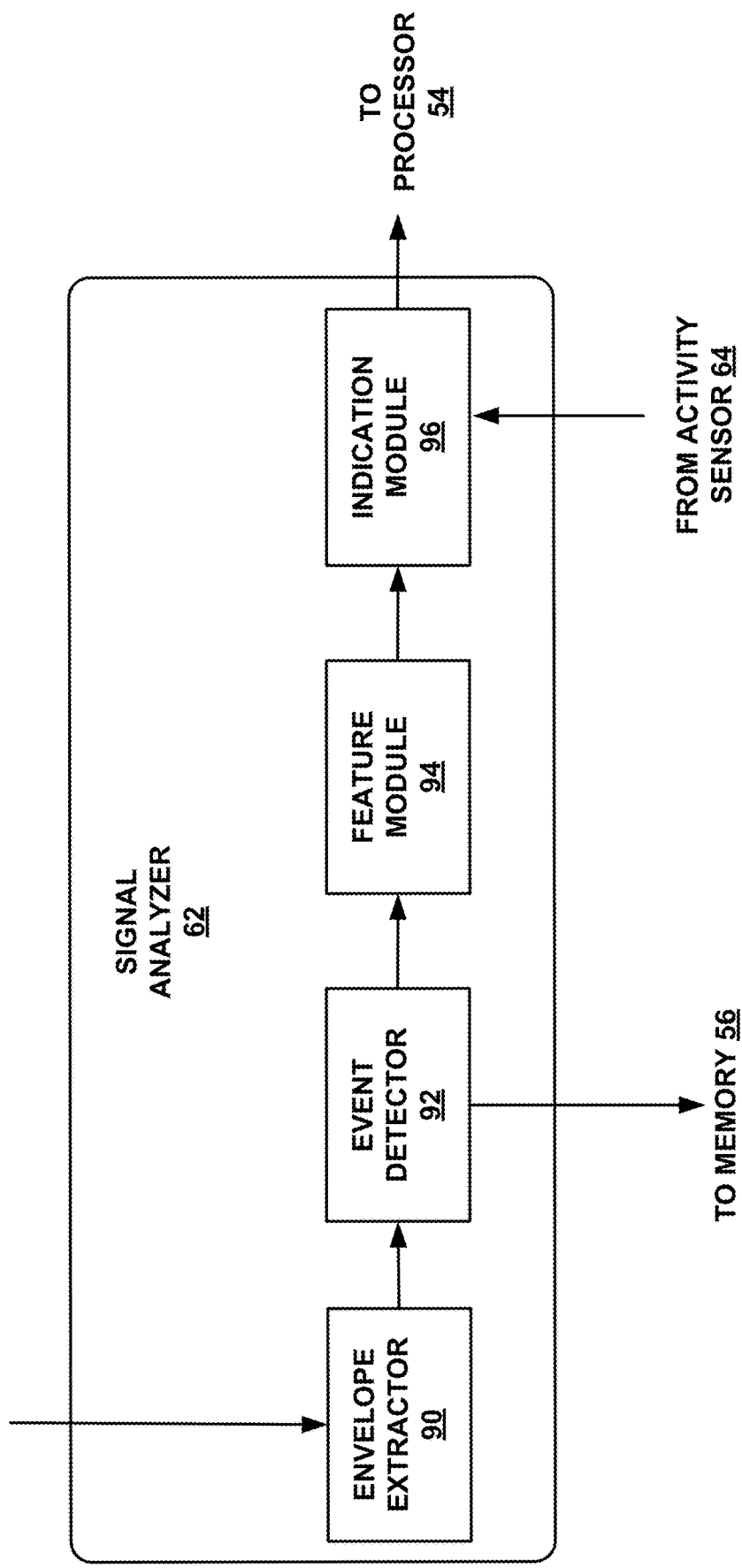
FIG. 6 is a functional block diagram illustrating an example configuration of a signal analyzer for analyzing an acoustic signal.

FIG. 6 is a functional block diagram illustrating an example configuration of signal analyzer 62. Although described as signal analyzer 62 of IMD 20, signal analyzer 46 functions in a similar manner. As illustrated in FIG. 6, signal analyzer 62 may include an envelope extractor 90, event detector 92, feature module 94, and indication module 96.

Envelope extractor 90 receives one or more electrical signals from acoustic sensor 16 and/or acoustic sensor 60. Each electrical signal may be digitized and parsed into segments of predetermined length. As an example, the electrical signal generated by acoustic sensor 60 may be sampled at a sampling rate of 200 Hertz (Hz) and parsed into segments including 100 or more sample points. Generally, envelope extractor 90 processes the received signal to extract an envelope, i.e., generate an envelope signal from the received signal.

In some examples, envelope extractor 90 operates to band pass filter, rectify and smooth the sensor signal before extracting the envelope signal. In examples where the prescription prescribes monitoring a heart sound signal, envelope extractor 90 may include a high pass filter, e.g., a 40 Hz high pass filter, and a low pass filter, such as a 70 Hz low pass filter, to remove unwanted signal components (e.g., above 70 Hz and below 40 Hz) from the acoustic signal. In some examples a first order infinite impulse response (IIR) high pass filter with a cutoff frequency of 40 Hz and a third order IIR low pass filter with a cutoff of 70 HZ may be used by envelope extractor 90. In some examples a band-pass filter with a 20 Hz high pass filter and a 70 Hz low pass filter is used by envelope extractor 90. In some examples, analog filtering of the acoustic signal may additionally or alternatively be performed prior to digitization of the signal and receipt by envelope extractor 90. As discussed above, IMD 20 may include analog-to digital conversion (ADC) circuitry. The filters used for each of the electrical signals from acoustic sensor 16 and acoustic sensor 60 may differ. The use of different filters may allow for different information of interest to be extracted from each signal. In some examples, the frequency of the acoustic signals may be separated into different bands by hardware or software filtering. For example, the bands may by 10-100 Hz, 100-1000 Hz, 1000-10,000 Hz, etc. Normal heart sounds, for example, have a frequency between 10-200 Hz. In some examples, where disease state is present, the heart sounds may have a frequency above the 10-200 Hz range. For normal heart sounds, the frequency of heart sound S1 is lower than heart sound S2. In addition, the frequency of respiration is much lower (e.g., 0.1-2 Hz) than normal heart sounds. This may be helpful in filtering out respiration effects. The use of different frequency bands based on the prescription, signal analyzer 62 may be able to extract information useful for determining if a change in patient state has occurred.

In some examples, a patient prescription may require monitoring of or detection of particular respiratory sounds. In such examples filtering may be used to detect the particular respiratory sounds. For example, in detecting wheezing, a band-pass filter may be used to isolate the sounds resulting from wheezing. Wheezes are generally a continuous sound that can be characterized by both pitch and duration. The dominate frequency of a wheeze may be approximately 400 Hz. Wheezes generally have a duration of greater than 100 milliseconds. In addition, both the fundamental and harmonic frequencies of acoustic signals associated with wheezes are greater than 100 Hz. Rhonchi is a low pitched wheeze with a duration of greater than 100 milliseconds and a frequency of greater than 300 Hz. The dominant frequency in the power spectrum of rhonchi is approximately 100 Hz. Crackles, on the other hand, are generally short and discontinuous sounds with a duration of less than 20 milliseconds. The different characteristics of known respiratory sounds may be used to determine appropriate filtering and detection of abnormal respiratory sounds.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In some examples, envelope extractor 90 may use other methods to generate the envelope signal, such as the normalized Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to event detector 92.

Event detector 92 utilizes an algorithm to detect various events within the envelope signal. The event detector 92 may be different for each type of electrical signal received. In some examples the event detector 92 identifies a plurality of sounds within each acoustic signal envelope to aid in the differentiation between the plurality of sounds in each acoustic signal. Generally, event detector 92 identifies the local maximums of the envelope signal. In order to identify the local maximums, event detector 92 may utilize an adaptively decaying threshold. The adaptively decaying threshold may be determined based on one or more of the running average of detected heart sound and/or cough amplitudes, the running average of the envelope signal amplitude, and the mean heart sound-to-heart sound or cough-to-cough interval. Event detector 92 compares the envelope signal to the adaptively decaying threshold to identify the local maximums. Event detector 92 may store markers, referred to as "event markers," for the identified local maximums within memory 72 or provide the event markers directly to feature module 94. Feature module 94 extracts features of the detected events.

Feature module 94 may process the acoustic signal in the frequency or time domain. Feature module 94 may confirm that an event detected by event detector 92 corresponds to the desired event. The desired event may be selected or programmed based on the patient prescription. For example, event detector 92 and feature module 94 may be programmed to detect and confirm events selected based on the patient prescription. The events may be used to track the progress of the condition of patient 12, which gave rise to the patient's prescription.

For example, a doctor may prescribe certain sounds to be tracked in order to follow a patient's current heart failure status. Based on the patient prescription, feature module 94 may confirm that an event detected by event detector 92 corresponds to the A2 heart sound, the P2 heart sound, or an identifiable lung sound, such as a cough. In some examples, feature module 94 may extract information from the heart sounds signal regarding the characteristics of a cough, for example. In some examples, feature module 94 may both confirm that an event detected by event detector 92 corresponds to a cough and extract information from the heart sounds signal regarding the characteristics of the cough.

Similarly, feature module 94 may both confirm that the event detected by event detector 92 corresponds to the A2 heart sound and extract information from the acoustic signal regarding the characteristics of the A2 heart sound. In examples where the feature module 94 extracts features in the frequency domain, feature module 94 may extract features including mean or median frequency, high frequency components, low frequency components, and high/low frequency components energy ratio. In some examples where feature module 94 extracts features of the time domain, feature module 94 may extract information regarding morphology of the A2 or P2 heart sound. Feature module 94 may extract information regarding duration and frequency of lung sound episodes or repetitiveness of coughing sounds episodes. Feature module 94 may also determine the depth a breath or the depth of an abnormal breathing sound such as a cough.

In some examples, various features may be determined based on comparison to a template. In some examples, various features may be determined using template matching schemes that compare signals associated with detected events to signals associated with template events, such as a wavelet template matching scheme or a "bounded template" matching scheme. An example wavelet template matching scheme is disclosed in U.S. Pat. No. 6,393,316 issued to Jeff Gillberg. An example bounded template matching scheme is disclosed in U.S. Patent Publication No. 20100185109, entitled "A Blurred Template Approach for Arrhythmia Detection," by Xin Zhang, Mark Brown, Xusheng Zhang, and Jeff Gillberg.

In some examples, template events used for determining various event features such as, in the example of cough detection, cough depth may be determined based on an example template loaded into feature module 94. In some examples, template events may be selected based on features specified by the patient prescription. In some examples, the templates may be patient specific. A baseline sound template may be collected for a particular sound to be monitored by acoustic sensor 16. The baseline may be collected when the feature is not present. In addition, a template may also be collected when a particular feature is present. For example, for cough detection, a baseline template may be the sound signal being collected when the patient is not coughing. This template may be used to help remove background noise that may be picked up by the acoustic sensor 16. A second template may be collected when a particular event is present. In some examples a plurality of templates may be collected, each associated with a specific characteristic observed by patient 12 or a physician, and probative of the condition of patient 12. In some examples, memory 56 stores acoustic signals collected during patient programming based on the patient prescription.

In some examples, feature module 94 may load different templates depending upon information from the activity/posture sensor 84. For example, in situations where the activity sensor 84 indicates that the patient 12 is laying down, the events may be compared to a different template than when patient 12 is propped up at an angle, and yet another template when the patient 12 is standing.

Indication module 96 receives information regarding various event features from feature module 94 and an activity signal from activity sensor 64. Based on the information from feature module 94 and activity sensor 64, indication module 96 may generate an indication that an event being monitored has occurred. In some examples, the indication may be generated based on the comparison of one or more of the inputs to a threshold.

In some examples, the indication of the event is provided to processor 54. Processor 54 may update a patient state based on the indication of the event from indication module 96. In some examples, indication module 96 may also provide indication of event severity to processor 54. The indication may be based in part of acoustic signal characteristics monitored by features module 94. In some examples, an indication of the event may incorporate information from activity sensor 64. For example, in instances where patient coughs are being monitored, an indication of a stronger cough may be made based on information from activity sensor 64 regarding chest movements. In some examples, processor 54 may increment an index associated with a particular condition being monitored upon receipt of an indication. Processor 54 may compare the index to a threshold that has been set based on the patient prescription.

Figure 7:
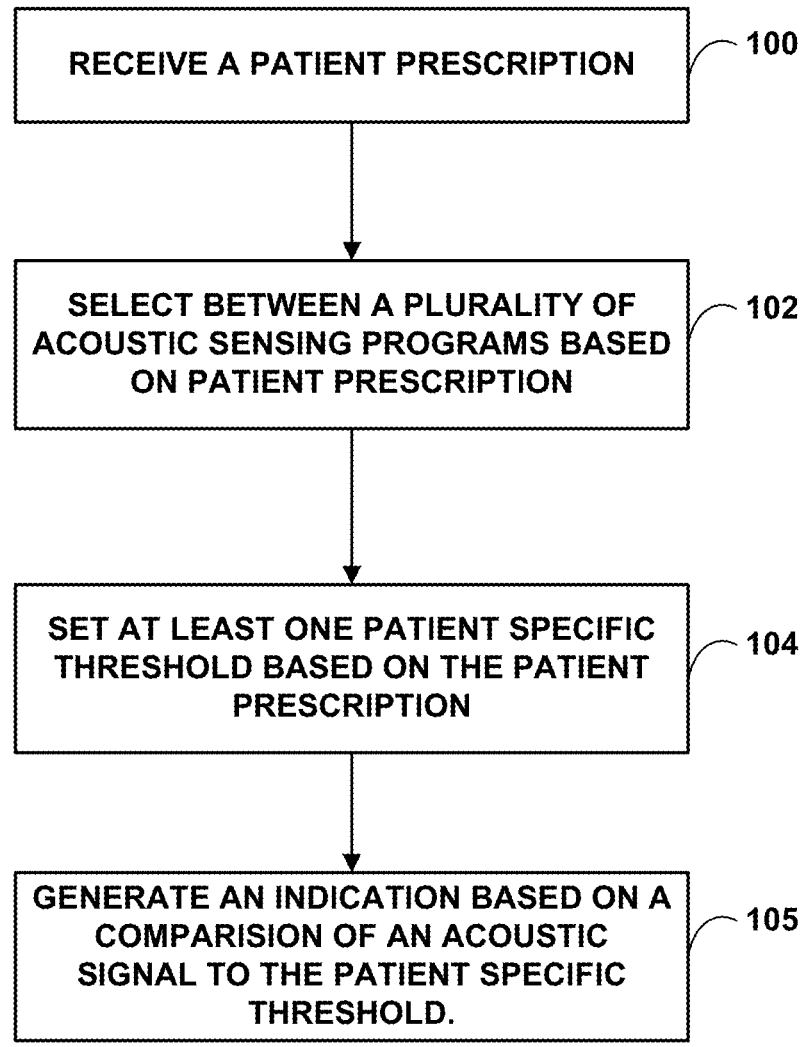
FIG. 7 is a flowchart illustrating an example method of programming an acoustic sensing device consistent with the present disclosure.

FIG. 7 is a flowchart illustrating an example method of programming an acoustic device consistent with the present disclosure. The acoustic sensing device may be an implantable medical device such as IMD 20, or an external device such as patch 14. A system 10 including at least one acoustic device receives a patient prescription (100). The prescription may be received by programmer 22 via user interface 50. In some examples, the patient prescription may be received by programmer 22, patch 14, or IMD 20 over network 28. Programmer 22, patch 14, or IMD 20, for example, selects between a plurality of acoustic sensing programs based on patient prescription (102). In some examples, processor 44 may select from a plurality of acoustic sensing programs stored in memory 48. In some examples, based on the patient prescription, the processor may select a subset of the plurality of acoustic sensing programs. For example, if patient 12 is at risk for heart failure, the patient prescription may include the selection of acoustic sensing programs to listen to both heart sounds and for various respiratory sounds which may indicate a change in heart failure. In other examples, the selected acoustic sensing program may sense a variety of acoustic signal characteristics or a variety of acoustic signals. The selected programs may include, for example, specific parameters for signal analyzer 62 including parameters for envelope extractor 90, event detector 92, feature module 94, and indication module 96.

Programmer 22 also sets at least one patient specific threshold based on the patient prescription (104). The patient specific threshold may be for a characteristic within the acoustic signal indicative of one or more symptoms. The patient specific threshold may be a threshold for indication module 96, for example. In some examples, the patient specific threshold is an indication threshold. In some examples, an indication threshold may be set for each of the sounds being monitored based on the selected acoustic sensing programs. In some examples, the indication threshold may be set based on a plurality of sensed acoustic signals or characteristics. The threshold may be set at a level which indicates that one of the current symptoms of patient 12 has progressed or changed by a predetermined amount. For example, the predetermined threshold may be set during programming. A baseline indicative of the patient's current state may be created during device programming. For example, a resting, baseline, respiratory rate of patient 12 may be determined based on a characteristic of the acoustic signal. A threshold for the patient may be set at a predetermined percentage change from the patient's resting, baseline, respiratory rate. In another example, a threshold may include a number of events over a predetermined time period. The predetermined time period may be a minute, an hour, a day, or a week, for example. In another example, the predetermined threshold may be based on a change in acoustic signal shape. For example, when the acoustic sensor 60 is monitoring vascular sounds, a baseline template for normal blood flow may be collected during initial programming.

In some examples, the threshold may be an indication threshold. An indication threshold may be set for a percentage deviation from the baseline template. Signal processor 62 may generate an indication based on a comparison of an acoustic signal to the patient specific threshold (105). In some examples, an indication from indication module 96 is sent to external programmer 22 when the acoustic signal indicates that the threshold has been crossed. The indication may indicate that a patient state has changed by a predetermined amount. In some examples the indication may be transmitted to a remote device along with a summary of acoustic signal data for review by a physician or other clinician or caregiver. In some examples, the physician may modify the prescription based on the indication.

Figure 8:
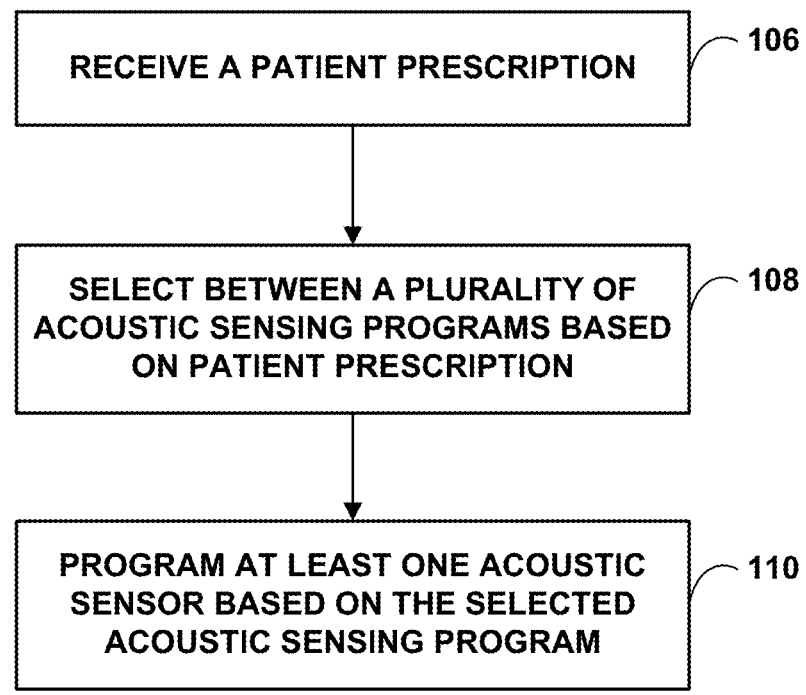
FIG. 8 is a flowchart illustrating an example method of programming an acoustic sensing device consistent with the present disclosure.

FIG. 8 an example method of programming an acoustic device consistent with the present disclosure. The acoustic device may be an implantable medical device such as IMD 20, or an external device such as patch 14. A system 10 including at least one acoustic device receives a patient prescription (106). The prescription may be received by programmer 22 via user interface 50. In some examples, the patient prescription may be received by programmer 22, patch 14, or IMD 20 over network 28. Programmer 22, patch 14, or IMD 20, for example, selects between a plurality of acoustic sensing programs based on patient prescription (108). In some examples, processor 44 may select from a plurality of acoustic sensing programs stored in memory 48. In some examples, based on the patient prescription, the processor may select a subset of the plurality of acoustic sensing programs. For example, if patient 12 is at risk for heart failure, the patient prescription may include the selection of acoustic sensing programs to listen to both heart sounds and for various respiratory sounds which may indicate a change in heart failure. In other examples, the selected acoustic sensing program may sense a variety of acoustic signals. The selected programs may include, for example, specifics for signal analyzer 62 including parameters for envelope extractor 90, event detector 92, feature module 94, and indication module 96. Programmer 22 also programs at least one acoustic sensor based on the selected acoustic sensing program (110). For example, programmer 22 may program acoustic sensor 60 to monitor and collect acoustic signals within a frequency range based on the acoustic sensing program.

Figure 9:
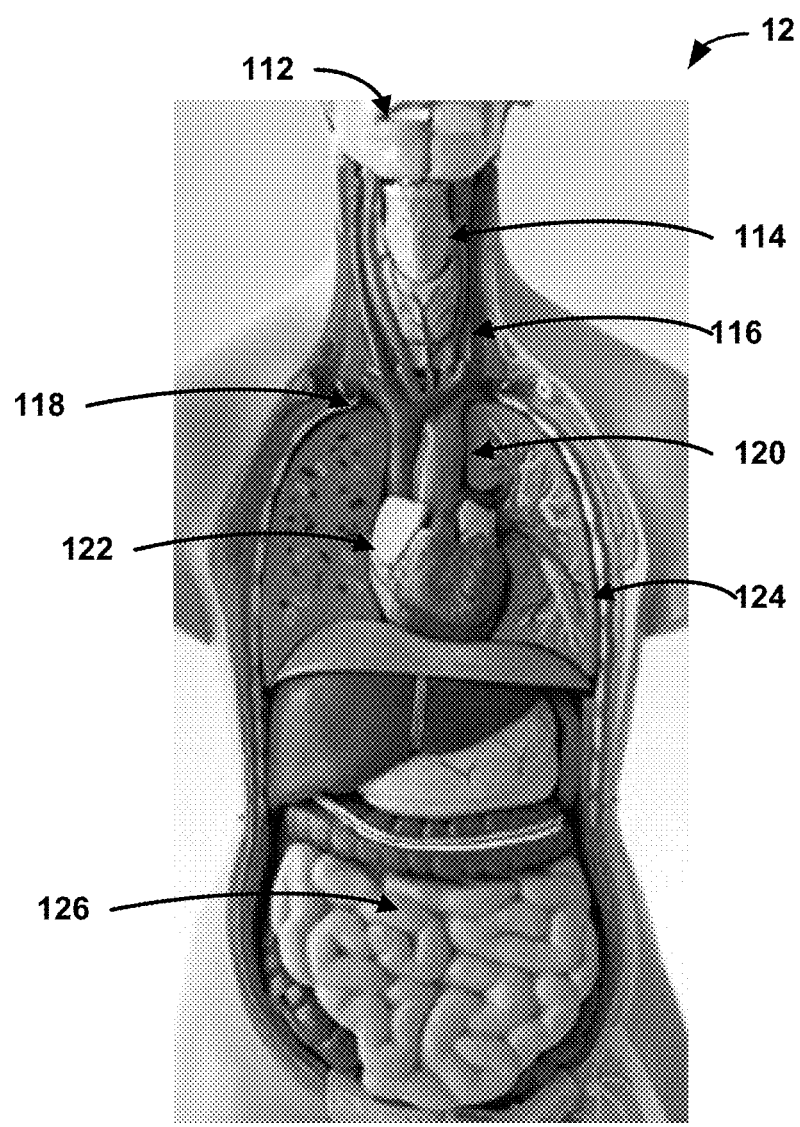
FIG. 9 is a diagram illustrating possible locations for placement of acoustic sensors on or within a body of a patient.

FIG. 9 is a diagram illustrating possible locations for placement acoustic sensors. In some examples, the acoustic sensors, such as acoustic sensor 60, may be placed internally, and in other examples, the acoustics sensor, such as acoustic sensor 16, may be placed externally proximate to the location shown in FIG. 9. Location 112 is near patient 12's jaw. An acoustic sensor at location 112 may collected voice commands, including for example, calls for help, living assistance or a voice diary. An acoustic sensor 60 at location 112 may pick up acoustic signals indicative of teeth grinding, bruxism, muscle spasms, or seizures. The acoustic signals collected at location 112 may be used to diagnose or monitory epilepsy or movement disorders, for example. One or more programs may be selected from memory 48 which include therapy programs such as frequencies to be monitored, or one or more templates to which the acoustic signal may be matched to perform detection, for example. In addition, at least one program may include a patient specific threshold for detection. The threshold may be set to detect when there has been predetermined amount of change in the patient's condition. In other examples, the threshold may be a particular sound signature, sure as "call 911." The patient specific threshold may be based on a patient specific voice recognition. In other examples, changes in voice patterns may be used to detect Parkinson's symptoms.

Location 114 is near the throat of patient 12. Acoustic signals collected by acoustic sensor 60 at location 114 may be used to detect things such as respiratory rate, pattern or cough, for example. Other respiratory sounds such as stridor, wheezing, crackles, rhonchi, Hamman's sign, pleural friction rub, fremitus, or bronchophonyathma may be detected by acoustic sensor 60 at location 124. Acoustic sensor 60 at location 124 may also detect respiratory rate, pattern or cough. The respiratory sounds may be used to tract the progression of, or detect the occurrence of, one or more respiratory states such as heart failure, pneumonia, asthma, apnea, tachypnea, bradypnea, asphyzia, Cheyne-Stokes respiration, for example.

Acoustic sensors 60 at locations 116, 118, and 120 may be used to detect acoustic signals indicative of vascular sounds. Location 116 may be proximate patient 12's jugular vein. Location 118 may be proximate the superior vena cava. Location 120 may be proximate to the aortic arch. The vascular sounds that may used to tract or detect intracranial vascular lesions, blood obstruction, stenosis, aneurysm, arteriovenous malformation, or fistulars, for example.

An acoustic sensor 60 at location 122 may be used to detect acoustic signals indicative of cardiac sounds such as heart sound signals S1-S4, heart murmur, pulse, gallop rhythm, or pericardial friction rub, for example. The cardiac sounds may be used to tract or detect valve disease, inflammation of the heart, or hear failure, for example.

An acoustic sensor 60 at location 126 may detect acoustic signals indicative gastrointestinal sounds such as stomach rumbles, growling, gurgling, or borborygmus, for example. The detected acoustic signals may be used to tract or diagnosis systems or diseases such as celiac, colitis, Irritable Bowel Syndrome, abdominal bloating, gastroparesis, or obstruction, for example.

An acoustic sensor 60 at location 127 may detect the acoustic signals for urination, including voiding frequency (day, night), voiding volume (low and short void event, indicative of a small bladder capacity), voiding difficulty (delayed, interrupted sound e.g. urethral obstruction), voiding efficacy and pattern et al. The detected acoustic signals may be used to examine bladder functions e.g. BPH, retention, nocturia, scale the severity of the disease.

The techniques described in this disclosure, including those attributed to programmer 22, IMD 20, external patch 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 54 of IMD 20, processor 52 or external patch 14, and/or processor 44 of programmer 22, any one or more parts of the techniques described herein may be implemented by a processor of one of external patch 14, IMD 20, programmer 22, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of have been described in this disclosure. These and other examples are within the scope of the following claims.

What is claimed is:
1. A method comprising:
receiving, by a processor, a patient prescription comprising information related to a selection of at least one acoustic sensing program to be performed for a patient based on a disease state of the patient;
selecting, by the processor, the at least one acoustic sensing program from a plurality of acoustic sensing programs based upon the information regarding the disease state of the patient as received in the patient prescription, each selected at least one acoustic program of the plurality of acoustic sensing programs associated with detection of at least one characteristic of a sensed acoustic signal associated with the disease state of the patient;
setting, by the processor, at least one patient specific threshold for the at least one characteristic of the sensed acoustic signal based on the patient prescription, wherein the patient specific threshold corresponds to a change in the disease state of the patient;
operating a medical device according to the selected at least one acoustic sensing program to sense, by at least one acoustic sensor, the acoustic signal;
receiving, by the processor, the sensed acoustic signal from the acoustic sensor;

analyzing, by the processor, the sensed acoustic signal using the selected at least one acoustic sensing program to detect a presence of the at least one characteristic in the sensed acoustic signal; and generating an indication associated with the disease state of the patient based on a comparison of the at least one characteristic of the sensed acoustic signal and the patient specific threshold.

2. The method of claim 1, further comprising programming the medical device based on the selected at least one acoustic sensing program.

3. The method of claim 1, further comprising indicating a location for placement of the at least one acoustic sensor based on the selected at least one acoustic sensing program.

4. The method of claim 1, further comprising selecting a subset of the plurality of acoustic sensing programs based on the patient prescription.

5. The method of claim 1, wherein the patient prescription is disease specific.

6. The method of claim 1, further comprising setting a plurality of patient specific thresholds based on the patient prescription.

7. The method of claim 6, further comprising
detecting the at least one characteristic of the sensed acoustic signal; and
comparing the at least one characteristic of the sensed acoustic signal to at least one of the plurality of patient specific thresholds;
wherein the plurality of patient specific thresholds provide a plurality of warning signals as a condition of the patient progresses.

8. The method of claim 1, further comprising
detecting a plurality of characteristics of the sensed acoustic signal; and
comparing each of the plurality of characteristics to a respective patient specific threshold.

9. The method of claim 1, further comprising:
transmitting the indication to a remote device.

10. The method of claim 1, wherein the indication indicates a change in the disease state of the patient.

11. A medical device system comprising:
an implantable telemetry module configured to receive a patient prescription comprising information related to a selection of at least one acoustic sensing program to be performed for a patient based on a disease state of the patient;
an acoustic sensor configured to sense an acoustic signal; and
a processor configured to:
select the at least one acoustic sensing program from a plurality of acoustic sensing programs based upon the information regarding the disease state of the patient as received in the patient prescription, each selected at least one acoustic sensing program of the plurality of acoustic sensing programs associated with detection of at least one characteristic of the sensed acoustic signal associated with the disease state of the patient;
set at least one patient specific threshold for the at least one characteristic of the sensed acoustic signal based on the patient prescription, wherein the patient specific threshold corresponds to a change in the disease state of the patient;
receive the sensed acoustic signal from the acoustic sensor;

analyze the sensed acoustic signal using the selected acoustic sensing program to detect a presence of the at least one characteristic in the sensed acoustic signal; and
generate an indication associated with the disease state of the patient based on a comparison of the at least one characteristic of the sensed acoustic signal and the patient specific threshold.

12. The medical device system of claim 11, wherein the acoustic sensor is an external sensor.

13. The medical device system of claim 11, wherein the acoustic sensor is an implantable sensor.

14. The medical device system of claim 13, further comprising an implantable medical device comprising the implantable sensor.

15. The medical device system of claim 13, further comprising a lead comprising the implantable sensor.

16. The medical device system of claim 11, further comprising a memory configured to store the plurality of acoustic sensing programs; and wherein the processor is further configured to select a subset of the plurality of acoustic sensing programs based on the received patient prescription.

17. The medical device system of claim 11, wherein the patient prescription is disease specific.

18. The medical device system of claim 11, wherein the processor is further configured to set a plurality of patient specific thresholds.

19. The medical device system of claim 18, wherein the processor is further configured to detect the at least one characteristic of the sensed acoustic signal, compare the at least on characteristics of the acoustic signal to at least one of the plurality of patient specific thresholds, and wherein the plurality of patient specific thresholds provide a plurality of warning signals as a condition of the patient progresses.

20. The medical device system of claim 11, wherein the processor is further configured to detect a plurality of characteristics of the sensed acoustic signal and compare each of the plurality of characteristics to a respective patient specific threshold, and generate the indication based on the comparisons.

21. The medical device system of claim 20, wherein the indication indicates a change in the disease state of the patient.

22. The medical device system of claim 11, further comprising a remote device, and wherein the implantable telemetry module is further configured to send the indication to the remote device.

23. The medical device system of claim 11, wherein detection of the presence of the at least one characteristic in the sensed acoustic signal comprises comparison of one or more features extracted from the sensed acoustic signal to a baseline sound template that is specific to the patient.

24. The medical device system of claim 11, wherein the information related to acoustic sensing to be performed for a patient is associated with one or more bladder functions of the patient, and the acoustic sensor is configured to provide the sensed acoustic signal based on one or more sensed urinary voiding sounds.

25. A system comprising:
implantable means for receiving a patient prescription comprising information related to a selection of at least one acoustic sensing program to be performed for a patient based on a disease state of the patient;
means for sensing an acoustic signal;
means for selecting the at least one acoustic sensing program from a plurality of acoustic sensing programs based upon the information regarding the disease state of the patient as received in the patient prescription, each selected at least one of the acoustic sensing program of the plurality of acoustic sensing programs associated with detection of at least one characteristic of the sensed acoustic signal associated with the disease state of the patient;

means for setting at least one patient specific threshold for the at least one characteristic of the sensed acoustic signal based on the patient prescription, wherein the patient specific threshold corresponds to a change in the disease state of the patient;

means for operating a medical device according to the selected at least one acoustic sensing program to receive the sensed acoustic signal and analyze the sensed acoustic signal using the selected acoustic sensing program to detect a presence of the at least one characteristic in the sensed acoustic signal; and means for generating an indication associated with the disease state of the patient based on a comparison of the at least one characteristic of the sensed acoustic signal and the patient specific threshold.

26. The system of claim 25, further comprising means for detecting the at least one characteristic of the sensed acoustic signal.

27. The system of claim 25, wherein the indication indicates a change in the disease state of the patient.

28. The medical device system of claim 11, wherein the processor is further configured to program the acoustic sensor to monitor and collect the sensed acoustic signal within a frequency range based on the selected acoustic sensing program.

* * * * *